United States Patent [19]

Isaac et al.

[11] Patent Number: 5,407,910
[45] Date of Patent: Apr. 18, 1995

[54] CYCLOPENT-1-EN-3,5-DIONE COMPOUNDS AND COMPOSITIONS

[75] Inventors: Benjamin O. Isaac, Ilford; Chat O. Chan, Ipswich; Ian M. Marr, Woodford Green, all of England

[73] Assignee: Union Camp Corporation, Princeton, N.J.

[21] Appl. No.: 134,920

[22] Filed: Oct. 12, 1993

[51] Int. Cl.$^6$ .............................................. A61K 7/46
[52] U.S. Cl. ........................................ 512/8; 568/379
[58] Field of Search ............................ 568/379; 512/8

[56] References Cited

U.S. PATENT DOCUMENTS

| | | | |
|---|---|---|---|
| 3,349,130 | 10/1967 | Bucoart et al. | 260/586 |
| 3,381,035 | 4/1968 | Miki et al. | 260/586 |
| 3,715,400 | 2/1973 | Kierstead et al. | 260/586 |
| 3,941,828 | 3/1976 | Buchi | 260/468 |
| 3,992,432 | 11/1976 | Napier et al. | 260/465.1 |
| 4,157,352 | 6/1979 | Brenner | 568/379 |
| 4,465,862 | 8/1984 | Saito et al. | 568/379 |
| 4,877,911 | 10/1989 | Frank | 585/411 |

OTHER PUBLICATIONS

Herrera et al, Chem. Abst., vol. 96, #122, 334q (1982).
Flament et al, Chem. Abst., vol. 91, #122, 292w (1979).
Clemo et al., "Synthesis of Calythrone and Related Cyclopentene-1,3-diones *via* Rearrangement of 4–Ylidenebutenolides", *J.C.S. Perkin I*, pp. 1448–1453 (1981).
Hirai et al., "Ruthenium Hydride–Catalyzed Double Bond Migration of 2,5-Dimethoxy-2,5-Dihydrofurans, A New Process for the Preparation of γ-Ketoesters", *Chemistry Letters*, pp. 23–26 (1982).
Jondiko et al., "A New Approach to Rehthrolone Synthesis", *Chem. Soc. Perkin Trans. I*, pp. 467–469 (1983).
*The Merck Index*, p. 754, Windholz, Martha, ed. (Merck & Co., Inc., Tenth Edition) (1983).
Secondini, "Handbook of Perfumes and Flavors", pp. 162–163, pp. 236–239 (Chemical Publishing Co., Inc., New York, N.Y.) (1990).

*Primary Examiner*—James H. Reamer
*Attorney, Agent, or Firm*—Woodcock, Washburn, Kurtz, Mackiewicz & Norris

[57] ABSTRACT

The present invention provides novel compounds such as 1,2-dimethyl-4-butyl-cyclopent-1-en-3,5-dione and 1,2-dimethyl-4,4-dibutyl-cyclopent-1-en-3,5-dione, having active floral-type aroma and methods for preparing same.

17 Claims, No Drawings

CYCLOPENT-1-EN-3,5-DIONE COMPOUNDS AND COMPOSITIONS

BACKGROUND OF THE INVENTION

The present invention relates to novel cyclopent-1-en-3,5-dione compounds and compositions having a fragrant floral-type aroma, and to processes for their preparation.

Floral-type fragrances are in great demand for use in various products such as in perfumes, colognes, cosmetics, soaps and others. For example, jasmine is the chemical constituent responsible for the odor produced by the jasmine flower. Fragrance chemists have spent considerable time searching for synthetic products which duplicate or closely simulate the natural jasmine-type scent, as well as other floral scents.

As a result of these research efforts, a number of different floral-type odorant compounds have been discovered. Chemicals for jasmine scent matching include acetate C-8, amyl cinnamic aldehyde, α-amyl cinnamic aldehyde dimethyl acetal, benzyl acetate, benzyl butyrate, benzyl isobutyrate, hexyl cinnamic aldehyde, indole, ionone, isojasmone, linalool and methyl anthranilate. O. Secondini, Handbook of Perfumes and Flavors (Chemical Publishing Co. 1990) at 163.

New and better floral-type aroma compounds are needed. The present invention is directed to this important end.

SUMMARY OF THE INVENTION
The present invention provides novel cyclopent-1-en-3,5-dione compounds of the formula [I]:

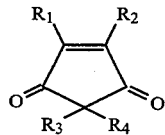

wherein
$R_1$ is H, $CH_3$, $CH_2CH_3$, $(CH_2)_2CH_3$, $(CH_2)_3CH_3$ or $(CH_2)_4CH_3$;
$R_2$ is H, $CH_3$, $CH_2CH_3$, $(CH_2)_2CH_3$, $(CH_2)_3CH_3$ or $(CH_2)_4CH_3$;
$R_3$ is H, $CH_3$, $CH_2CH_3$, $(CH_2)_2CH_3$, $(CH_2)_3CH_3$, $(CH_2)_4CH_3$ or $CH_2CH=CHCH_2CH_3$, and
$R_4$ is H, $CH_3$, $CH_2CH_3$, $(CH_2)_2CH_3$, $(CH_2)_3CH_3$, $(CH_2)_4CH_3$ or $CH_2CH=CHCH_2CH_3$;
provided that when one of $R_3$ or $R_4$ is H, then the other of $R_3$ or $R_4$ is $CH_3$, $CH_2CH_3$, $(CH_2)_2CH_3$, $(CH_2)_3CH_3$, $(CH_2)_4CH_3$ or $CH_2CH=CHCH_2CH_3$.

The foregoing formula [I] compounds possess active floral-type aroma fragrances having utility in the perfumery and/or other industries. The compounds of the invention can be used alone or in combination with other compounds or ingredients, and thus the present invention is further directed to the use of compounds in combination with carriers and/or additional perfumery ingredients as fragrance compositions, as well as methods for their preparation.

DETAILED DESCRIPTION OF THE INVENTION

As noted above, the present invention is directed to novel jasmine-type compounds of the formula [I]:

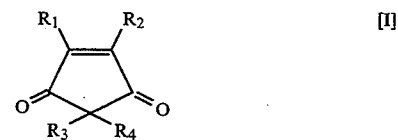

wherein
$R_1$ is H, $CH_3$, $CH_2CH_3$, $(CH_2)_2CH_3$, $(CH_2)_3CH_3$ or $(CH_2)_4CH_3$;
$R_2$ is H, $CH_3$, $CH_2CH_3$, $(CH_2)_2CH_3$, $(CH_2)_3CH_3$ or $(CH_2)_4CH_3$;
$R_3$ is H, $CH_3$, $CH_2CH_3$, $(CH_2)_2CH_3$, $(CH_2)_3CH_3$, $(CH_2)_4CH_3$ or $CH_2CH=CHCH_2CH_3$; and
$R_4$ is H, $CH_3$, $CH_2CH_3$, $(CH_2)_2CH_3$, $(CH_2)_3CH_3$, $(CH_2)_4CH_3$ or $CH_2CH=CHCH_2CH_3$;
provided that when one of $R_3$ or $R_4$ is H, then the other of $R_3$ or $R_4$ is $CH_3$, $CH_2CH_3$, $(CH_2)_2CH_3$, $(CH_2)_3CH_3$, $(CH_2)_4CH_3$ or $CH_2CH=CHCH_2CH_3$.

In the formula [I] compounds, preferably, $R_1$ and/or $R_2$ are $CH_3$, and most preferably both $R_1$ and $R_2$ are $CH_3$. Also, preferably $R_3$ and/or $R_4$ are $(CH_2)_3CH_3$. The most preferred formula [I] compounds are 1,2-dimethyl-4-butyl-cyclopent-1-en-3,5-dione and 1,2-dimethyl-4,4-dibutyl-cyclopent-1-en-3,5-dione, especially 1,2-dimethyl-4-butyl-cyclopent-1-en-3,5-dione. Various representative compounds within the scope of formula [I] are set forth in Table I below.

TABLE I

| $R_1$ | $R_2$ | $R_3$ | $R_4$ |
|---|---|---|---|
| H | H | $CH_3$ | H |
| H | H | $CH_3$ | $CH_3$ |
| H | H | $CH_2CH_3$ | H |
| H | H | $CH_2CH_3$ | $CH_2CH_3$ |
| H | H | $(CH_2)_2CH_3$ | H |
| H | H | $(CH_2)_2CH_3$ | $(CH_2)_2CH_3$ |
| H | H | $(CH_2)_3CH_3$ | H |
| H | H | $(CH_2)_3CH_3$ | $(CH_2)_3CH_3$ |
| H | H | $(CH_2)_4CH_3$ | H |
| H | H | $(CH_2)_4CH_3$ | $(CH_2)_4CH_3$ |
| H | H | $CH_2CH=CHCH_2CH_3$ | H |
| H | H | $CH_2CH=CHCH_2CH_3$ | $CH_2CH=CHCH_2CH_3$ |
| H | $CH_3$ | $CH_3$ | H |
| H | $CH_3$ | $CH_3$ | $CH_3$ |
| H | $CH_3$ | $CH_2CH_3$ | H |
| H | $CH_3$ | $CH_2CH_3$ | $CH_2CH_3$ |
| H | $CH_3$ | $(CH_2)_2CH_3$ | H |
| H | $CH_3$ | $(CH_2)_2CH_3$ | $(CH_2)_2CH_3$ |
| H | $CH_3$ | $(CH_2)_3CH_3$ | H |
| H | $CH_3$ | $(CH_2)_3CH_3$ | $(CH_2)_3CH_3$ |
| H | $CH_3$ | $(CH_2)_4CH_3$ | H |

TABLE I-continued

| R₁ | R₂ | R₃ | R₄ |
|---|---|---|---|
| H | CH₃ | (CH₂)₄CH₃ | (CH₂)₄CH₃ |
| H | CH₃ | CH₂CH=CHCH₂CH₃ | H |
| H | CH₃ | CH₂CH=CHCH₂CH₃ | CH₂CH=CHCH₂CH₃ |
| CH₃ | H | CH₃ | H |
| CH₃ | H | CH₃ | CH₃ |
| CH₃ | H | CH₂CH₃ | H |
| CH₃ | H | CH₂CH₃ | CH₂CH₃ |
| CH₃ | H | (CH₂)₂CH₃ | H |
| CH₃ | H | (CH₂)₂CH₃ | (CH₂)₂CH₃ |
| CH₃ | H | (CH₂)₃CH₃ | H |
| CH₃ | H | (CH₂)₃CH₃ | (CH₂)₃CH₃ |
| CH₃ | H | (CH₂)₄CH₃ | H |
| CH₃ | H | (CH₂)₄CH₃ | (CH₂)₄CH₃ |
| CH₃ | H | CH₂CH=CHCH₂CH₃ | H |
| CH₃ | H | CH₂CH=CHCH₂CH₃ | CH₂CH=CHCH₂CH₃ |
| CH₃ | CH₃ | CH₃ | H |
| CH₃ | CH₃ | CH₃ | CH₃ |
| CH₃ | CH₃ | CH₂CH₃ | H |
| CH₃ | CH₃ | CH₂CH₃ | CH₂CH₃ |
| CH₃ | CH₃ | (CH₂)₂CH₃ | H |
| CH₃ | CH₃ | (CH₂)₂CH₃ | (CH₂)₂CH₃ |
| CH₃ | CH₃ | (CH₂)₃CH₃ | H |
| CH₃ | CH₃ | (CH₂)₃CH₃ | (CH₂)₃CH₃ |
| CH₃ | CH₃ | (CH₂)₄CH₃ | H |
| CH₃ | CH₃ | (CH₂)₄CH₃ | (CH₂)₄CH₃ |
| CH₃ | CH₃ | CH₂CH=CHCH₂CH₃ | H |
| CH₃ | CH₃ | CH₂CH=CHCH₂CH₃ | CH₂CH=CHCH₂CH₃ |
| H | CH₂CH₃ | CH₃ | H |
| H | CH₂CH₃ | CH₃ | CH₃ |
| H | CH₂CH₃ | CH₂CH₃ | H |
| H | CH₂CH₃ | CH₂CH₃ | CH₂CH₃ |
| H | CH₂CH₃ | (CH₂)₂CH₃ | H |
| H | CH₂CH₃ | (CH₂)₂CH₃ | (CH₂)₂CH₃ |
| H | CH₂CH₃ | (CH₂)₃CH₃ | H |
| H | CH₂CH₃ | (CH₂)₃CH₃ | (CH₂)₃CH₃ |
| H | CH₂CH₃ | (CH₂)₄CH₃ | H |
| H | CH₂CH₃ | (CH₂)₄CH₃ | (CH₂)₄CH₃ |
| H | CH₂CH₃ | CH₂CH=CHCH₂CH₃ | H |
| H | CH₂CH₃ | CH₂CH=CHCH₂CH₃ | CH₂CH=CHCH₂CH₃ |
| CH₂CH₃ | H | CH₃ | H |
| CH₂CH₃ | H | CH₃ | CH₃ |
| CH₂CH₃ | H | CH₂CH₃ | H |
| CH₂CH₃ | H | CH₂CH₃ | CH₂CH₃ |
| CH₂CH₃ | H | (CH₂)₂CH₃ | H |
| CH₂CH₃ | H | (CH₂)₂CH₃ | (CH₂)₂CH₃ |
| CH₂CH₃ | H | (CH₂)₃CH₃ | H |
| CH₂CH₃ | H | (CH₂)₃CH₃ | (CH₂)₃CH₃ |
| CH₂CH₃ | H | (CH₂)₄CH₃ | H |
| CH₂CH₃ | H | (CH₂)₄CH₃ | (CH₂)₄CH₃ |
| CH₂CH₃ | H | CH₂CH=CHCH₂CH₃ | H |
| CH₂CH₃ | H | CH₂CH=CHCH₂CH₃ | CH₂CH=CHCH₂CH₃ |
| CH₃ | CH₂CH₃ | CH₃ | H |
| CH₃ | CH₂CH₃ | CH₃ | CH₃ |
| CH₃ | CH₂CH₃ | CH₂CH₃ | H |
| CH₃ | CH₂CH₃ | CH₂CH₃ | CH₂CH₃ |
| CH₃ | CH₂CH₃ | (CH₂)₂CH₃ | H |
| CH₃ | CH₂CH₃ | (CH₂)₂CH₃ | (CH₂)₂CH₃ |
| CH₃ | CH₂CH₃ | (CH₂)₃CH₃ | H |
| CH₃ | CH₂CH₃ | (CH₂)₃CH₃ | (CH₂)₃CH₃ |
| CH₃ | CH₂CH₃ | (CH₂)₄CH₃ | H |
| CH₃ | CH₂CH₃ | (CH₂)₄CH₃ | (CH₂)₄CH₃ |
| CH₃ | CH₂CH₃ | CH₂CH=CHCH₂CH₃ | H |
| CH₃ | CH₂CH₃ | CH₂CH=CHCH₂CH₃ | CH₂CH=CHCH₂CH₃ |
| CH₂CH₃ | CH₃ | CH₃ | H |
| CH₂CH₃ | CH₃ | CH₃ | CH₃ |
| CH₂CH₃ | CH₃ | CH₂CH₃ | H |
| CH₂CH₃ | CH₃ | CH₂CH₃ | CH₂CH₃ |
| CH₂CH₃ | CH₃ | (CH₂)₂CH₃ | H |
| CH₂CH₃ | CH₃ | (CH₂)₂CH₃ | (CH₂)₂CH₃ |
| CH₂CH₃ | CH₃ | (CH₂)₃CH₃ | H |
| CH₂CH₃ | CH₃ | (CH₂)₃CH₃ | (CH₂)₃CH₃ |
| CH₂CH₃ | CH₃ | (CH₂)₄CH₃ | H |
| CH₂CH₃ | CH₃ | (CH₂)₄CH₃ | (CH₂)₄CH₃ |
| CH₂CH₃ | CH₃ | CH₂CH=CHCH₂CH₃ | H |
| CH₂CH₃ | CH₃ | CH₂CH=CHCH₂CH₃ | CH₂CH=CHCH₂CH₃ |
| CH₂CH₃ | CH₂CH₃ | CH₃ | H |
| CH₂CH₃ | CH₂CH₃ | CH₃ | CH₃ |
| CH₂CH₃ | CH₂CH₃ | CH₂CH₃ | H |
| CH₂CH₃ | CH₂CH₃ | CH₂CH₃ | CH₂CH₃ |
| CH₂CH₃ | CH₂CH₃ | (CH₂)₂CH₃ | H |
| CH₂CH₃ | CH₂CH₃ | (CH₂)₂CH₃ | (CH₂)₂CH₃ |

TABLE I-continued

| R₁ | R₂ | R₃ | R₄ |
|---|---|---|---|
| CH₂CH₃ | CH₂CH₃ | (CH₂)₃CH₃ | H |
| CH₂CH₃ | CH₂CH₃ | (CH₂)₃CH₃ | (CH₂)₃CH₃ |
| CH₂CH₃ | CH₂CH₃ | (CH₂)₄CH₃ | H |
| CH₂CH₃ | CH₂CH₃ | (CH₂)₄CH₃ | (CH₂)₄CH₃ |
| CH₂CH₃ | CH₂CH₃ | CH₂CH=CHCH₂CH₃ | H |
| CH₂CH₃ | CH₂CH₃ | CH₂CH=CHCH₂CH₃ | CH₂CH=CHCH₂CH₃ |
| H | (CH₂)₂CH₃ | CH₃ | H |
| H | (CH₂)₂CH₃ | CH₃ | CH₃ |
| H | (CH₂)₂CH₃ | CH₂CH₃ | H |
| H | (CH₂)₂CH₃ | CH₂CH₃ | CH₂CH₃ |
| H | (CH₂)₂CH₃ | (CH₂)₂CH₃ | H |
| H | (CH₂)₂CH₃ | (CH₂)₂CH₃ | (CH₂)₂CH₃ |
| H | (CH₂)₂CH₃ | (CH₂)₃CH₃ | H |
| H | (CH₂)₂CH₃ | (CH₂)₃CH₃ | (CH₂)₃CH₃ |
| H | (CH₂)₂CH₃ | (CH₂)₄CH₃ | H |
| H | (CH₂)₂CH₃ | (CH₂)₄CH₃ | (CH₂)₄CH₃ |
| H | (CH₂)₂CH₃ | CH₂CH=CHCH₂CH₃ | H |
| H | (CH₂)₂CH₃ | CH₂CH=CHCH₂CH₃ | CH₂CH=CHCH₂CH₃ |
| (CH₂)₂CH₃ | H | CH₃ | H |
| (CH₂)₂CH₃ | H | CH₃ | CH₃ |
| (CH₂)₂CH₃ | H | CH₂CH₃ | H |
| (CH₂)₂CH₃ | H | CH₂CH₃ | CH₂CH₃ |
| (CH₂)₂CH₃ | H | (CH₂)₂CH₃ | H |
| (CH₂)₂CH₃ | H | (CH₂)₂CH₃ | (CH₂)₂CH₃ |
| (CH₂)₂CH₃ | H | (CH₂)₃CH₃ | H |
| (CH₂)₂CH₃ | H | (CH₂)₃CH₃ | (CH₂)₃CH₃ |
| (CH₂)₂CH₃ | H | (CH₂)₄CH₃ | H |
| (CH₂)₂CH₃ | H | (CH₂)₄CH₃ | (CH₂)₄CH₃ |
| (CH₂)₂CH₃ | H | CH₂CH=CHCH₂CH₃ | H |
| (CH₂)₂CH₃ | H | CH₂CH=CHCH₂CH₃ | CH₂CH=CHCH₂CH₃ |
| CH₃ | (CH₂)₂CH₃ | CH₃ | H |
| CH₃ | (CH₂)₂CH₃ | CH₃ | CH₃ |
| CH₃ | (CH₂)₂CH₃ | CH₂CH₃ | H |
| CH₃ | (CH₂)₂CH₃ | CH₂CH₃ | CH₂CH₃ |
| CH₃ | (CH₂)₂CH₃ | (CH₂)₂CH₃ | H |
| CH₃ | (CH₂)₂CH₃ | (CH₂)₂CH₃ | (CH₂)₂CH₃ |
| CH₃ | (CH₂)₂CH₃ | (CH₂)₃CH₃ | H |
| CH₃ | (CH₂)₂CH₃ | (CH₂)₃CH₃ | (CH₂)₃CH₃ |
| CH₃ | (CH₂)₂CH₃ | (CH₂)₄CH₃ | H |
| CH₃ | (CH₂)₂CH₃ | (CH₂)₄CH₃ | (CH₂)₄CH₃ |
| CH₃ | (CH₂)₂CH₃ | CH₂CH=CHCH₂CH₃ | H |
| CH₃ | (CH₂)₂CH₃ | CH₂CH=CHCH₂CH₃ | CH₂CH=CHCH₂CH₃ |
| (CH₂)₂CH₃ | CH₃ | CH₃ | H |
| (CH₂)₂CH₃ | CH₃ | CH₃ | CH₃ |
| (CH₂)₂CH₃ | CH₃ | CH₂CH₃ | H |
| (CH₂)₂CH₃ | CH₃ | CH₂CH₃ | CH₂CH₃ |
| (CH₂)₂CH₃ | CH₃ | (CH₂)₂CH₃ | H |
| (CH₂)₂CH₃ | CH₃ | (CH₂)₂CH₃ | (CH₂)₂CH₃ |
| (CH₂)₂CH₃ | CH₃ | (CH₂)₃CH₃ | H |
| (CH₂)₂CH₃ | CH₃ | (CH₂)₃CH₃ | (CH₂)₃CH₃ |
| (CH₂)₂CH₃ | CH₃ | (CH₂)₄CH₃ | H |
| (CH₂)₂CH₃ | CH₃ | (CH₂)₄CH₃ | (CH₂)₄CH₃ |
| (CH₂)₂CH₃ | CH₃ | CH₂CH=CHCH₂CH₃ | H |
| (CH₂)₂CH₃ | CH₃ | CH₂CH=CHCH₂CH₃ | CH₂CH=CHCH₂CH₃ |
| CH₂CH₃ | (CH₂)₂CH₃ | CH₃ | H |
| CH₂CH₃ | (CH₂)₂CH₃ | CH₃ | CH₃ |
| CH₂CH₃ | (CH₂)₂CH₃ | CH₂CH₃ | H |
| CH₂CH₃ | (CH₂)₂CH₃ | CH₂CH₃ | CH₂CH₃ |
| CH₂CH₃ | (CH₂)₂CH₃ | (CH₂)₂CH₃ | H |
| CH₂CH₃ | (CH₂)₂CH₃ | (CH₂)₂CH₃ | (CH₂)₂CH₃ |
| CH₂CH₃ | (CH₂)₂CH₃ | (CH₂)₃CH₃ | H |
| CH₂CH₃ | (CH₂)₂CH₃ | (CH₂)₃CH₃ | (CH₂)₃CH₃ |
| CH₂CH₃ | (CH₂)₂CH₃ | (CH₂)₄CH₃ | H |
| CH₂CH₃ | (CH₂)₂CH₃ | (CH₂)₄CH₃ | (CH₂)₄CH₃ |
| CH₂CH₃ | (CH₂)₂CH₃ | CH₂CH=CHCH₂CH₃ | H |
| CH₂CH₃ | (CH₂)₂CH₃ | CH₂CH=CHCH₂CH₃ | CH₂CH=CHCH₂CH₃ |
| (CH₂)₂CH₃ | CH₂CH₃ | CH₃ | H |
| (CH₂)₂CH₃ | CH₂CH₃ | CH₃ | CH₃ |
| (CH₂)₂CH₃ | CH₂CH₃ | CH₂CH₃ | H |
| (CH₂)₂CH₃ | CH₂CH₃ | CH₂CH₃ | CH₂CH₃ |
| (CH₂)₂CH₃ | CH₂CH₃ | (CH₂)₂CH₃ | H |
| (CH₂)₂CH₃ | CH₂CH₃ | (CH₂)₂CH₃ | (CH₂)₂CH₃ |
| (CH₂)₂CH₃ | CH₂CH₃ | (CH₂)₃CH₃ | H |
| (CH₂)₂CH₃ | CH₂CH₃ | (CH₂)₃CH₃ | (CH₂)₃CH₃ |
| (CH₂)₂CH₃ | CH₂CH₃ | (CH₂)₄CH₃ | H |
| (CH₂)₂CH₃ | CH₂CH₃ | (CH₂)₄CH₃ | (CH₂)₄CH₃ |
| (CH₂)₂CH₃ | CH₂CH₃ | CH₂CH=CHCH₂CH₃ | H |
| (CH₂)₂CH₃ | CH₂CH₃ | CH₂CH=CHCH₂CH₃ | CH₂CH=CHCH₂CH₃ |
| (CH₂)₂CH₃ | (CH₂)₂CH₃ | CH₃ | H |
| (CH₂)₂CH₃ | (CH₂)₂CH₃ | CH₃ | CH₃ |
| (CH₂)₂CH₃ | (CH₂)₂CH₃ | CH₂CH₃ | H |

TABLE I-continued

| R₁ | R₂ | R₃ | R₄ |
|---|---|---|---|
| (CH₂)₂CH₃ | (CH₂)₂CH₃ | CH₂CH₃ | CH₂CH₃ |
| (CH₂)₂CH₃ | (CH₂)₂CH₃ | (CH₂)₂CH₃ | H |
| (CH₂)₂CH₃ | (CH₂)₂CH₃ | (CH₂)₂CH₃ | (CH₂)₂CH₃ |
| (CH₂)₂CH₃ | (CH₂)₂CH₃ | (CH₂)₃CH₃ | H |
| (CH₂)₂CH₃ | (CH₂)₂CH₃ | (CH₂)₃CH₃ | (CH₂)₃CH₃ |
| (CH₂)₂CH₃ | (CH₂)₂CH₃ | (CH₂)₄CH₃ | H |
| (CH₂)₂CH₃ | (CH₂)₂CH₃ | (CH₂)₄CH₃ | (CH₂)₄CH₃ |
| (CH₂)₂CH₃ | (CH₂)₂CH₃ | CH₂CH=CHCH₂CH₃ | H |
| (CH₂)₂CH₃ | (CH₂)₂CH₃ | CH₂CH=CHCH₂CH₃ | CH₂CH=CHCH₂CH₃ |
| H | (CH₂)₃CH₃ | CH₃ | H |
| H | (CH₂)₃CH₃ | CH₃ | CH₃ |
| H | (CH₂)₃CH₃ | CH₂CH₃ | H |
| H | (CH₂)₃CH₃ | CH₂CH₃ | CH₂CH₃ |
| H | (CH₂)₃CH₃ | (CH₂)₂CH₃ | H |
| H | (CH₂)₃CH₃ | (CH₂)₂CH₃ | (CH₂)₂CH₃ |
| H | (CH₂)₃CH₃ | (CH₂)₃CH₃ | H |
| H | (CH₂)₃CH₃ | (CH₂)₃CH₃ | (CH₂)₃CH₃ |
| H | (CH₂)₃CH₃ | (CH₂)₄CH₃ | H |
| H | (CH₂)₃CH₃ | (CH₂)₄CH₃ | (CH₂)₄CH₃ |
| H | (CH₂)₃CH₃ | CH₂CH=CHCH₂CH₃ | H |
| H | (CH₂)₃CH₃ | CH₂CH=CHCH₂CH₃ | CH₂CH=CHCH₂CH₃ |
| (CH₂)₃CH₃ | H | CH₃ | H |
| (CH₂)₃CH₃ | H | CH₃ | CH₃ |
| (CH₂)₃CH₃ | H | CH₂CH₃ | H |
| (CH₂)₃CH₃ | H | CH₂CH₃ | CH₂CH₃ |
| (CH₂)₃CH₃ | H | (CH₂)₂CH₃ | H |
| (CH₂)₃CH₃ | H | (CH₂)₂CH₃ | (CH₂)₂CH₃ |
| (CH₂)₃CH₃ | H | (CH₂)₃CH₃ | H |
| (CH₂)₃CH₃ | H | (CH₂)₃CH₃ | (CH₂)₃CH₃ |
| (CH₂)₃CH₃ | H | (CH₂)₄CH₃ | H |
| (CH₂)₃CH₃ | H | (CH₂)₄CH₃ | (CH₂)₄CH₃ |
| (CH₂)₃CH₃ | H | CH₂CH=CHCH₂CH₃ | H |
| (CH₂)₃CH₃ | H | CH₂CH=CHCH₂CH₃ | CH₂CH=CHCH₂CH₃ |
| CH₃ | (CH₂)₃CH₃ | CH₃ | H |
| CH₃ | (CH₂)₃CH₃ | CH₃ | CH₃ |
| CH₃ | (CH₂)₃CH₃ | CH₂CH₃ | H |
| CH₃ | (CH₂)₃CH₃ | CH₂CH₃ | CH₂CH₃ |
| CH₃ | (CH₂)₃CH₃ | (CH₂)₂CH₃ | H |
| CH₃ | (CH₂)₃CH₃ | (CH₂)₂CH₃ | (CH₂)₂CH₃ |
| CH₃ | (CH₂)₃CH₃ | (CH₂)₃CH₃ | H |
| CH₃ | (CH₂)₃CH₃ | (CH₂)₃CH₃ | (CH₂)₃CH₃ |
| CH₃ | (CH₂)₃CH₃ | (CH₂)₄CH₃ | H |
| CH₃ | (CH₂)₃CH₃ | (CH₂)₄CH₃ | (CH₂)₄CH₃ |
| CH₃ | (CH₂)₃CH₃ | CH₂CH=CHCH₂CH₃ | H |
| CH₃ | (CH₂)₃CH₃ | CH₂CH=CHCH₂CH₃ | CH₂CH=CHCH₂CH₃ |
| (CH₂)₃CH₃ | CH₃ | CH₃ | H |
| (CH₂)₃CH₃ | CH₃ | CH₃ | CH₃ |
| (CH₂)₃CH₃ | CH₃ | CH₂CH₃ | H |
| (CH₂)₃CH₃ | CH₃ | CH₂CH₃ | CH₂CH₃ |
| (CH₂)₃CH₃ | CH₃ | (CH₂)₂CH₃ | H |
| (CH₂)₃CH₃ | CH₃ | (CH₂)₂CH₃ | (CH₂)₂CH₃ |
| (CH₂)₃CH₃ | CH₃ | (CH₂)₃CH₃ | H |
| (CH₂)₃CH₃ | CH₃ | (CH₂)₃CH₃ | (CH₂)₃CH₃ |
| (CH₂)₃CH₃ | CH₃ | (CH₂)₄CH₃ | H |
| (CH₂)₃CH₃ | CH₃ | (CH₂)CH₃ | (CH₂)₄CH₃ |
| (CH₂)₃CH₃ | CH₃ | CH₂CH=CHCH₂CH₃ | H |
| (CH₂)₃CH₃ | CH₃ | CH₂CH=CHCH₂CH₃ | CH₂CH=CHCH₂CH₃ |
| CH₂CH₃ | (CH₂)₃CH₃ | CH₃ | H |
| CH₂CH₃ | (CH₂)₃CH₃ | CH₃ | CH₃ |
| CH₂CH₃ | (CH₂)₃CH₃ | CH₂CH₃ | H |
| CH₂CH₃ | (CH₂)₃CH₃ | CH₂CH₃ | CH₂CH₃ |
| CH₂CH₃ | (CH₂)₃CH₃ | (CH₂)₂CH₃ | H |
| CH₂CH₃ | (CH₂)₃CH₃ | (CH₂)₂CH₃ | (CH₂)₂CH₃ |
| CH₂CH₃ | (CH₂)₃CH₃ | (CH₂)₃CH₃ | H |
| CH₂CH₃ | (CH₂)₃CH₃ | (CH₂)₃CH₃ | (CH₂)₃CH₃ |
| CH₂CH₃ | (CH₂)₃CH₃ | (CH₂)₄CH₃ | H |
| CH₂CH₃ | (CH₂)₃CH₃ | (CH₂)₄CH₃ | (CH₂)₄CH₃ |
| CH₂CH₃ | (CH₂)₃CH₃ | CH₂CH=CHCH₂CH₃ | H |
| CH₂CH₃ | (CH₂)₃CH₃ | CH₂CH=CHCH₂CH₃ | CH₂CH=CHCH₂CH₃ |
| (CH₂)₃CH₃ | CH₂CH₃ | CH₃ | H |
| (CH₂)₃CH₃ | CH₂CH₃ | CH₃ | CH₃ |
| (CH₂)₃CH₃ | CH₂CH₃ | CH₂CH₃ | H |
| (CH₂)₃CH₃ | CH₂CH₃ | CH₂CH₃ | CH₂CH₃ |
| (CH₂)₃CH₃ | CH₂CH₃ | (CH₂)₂CH₃ | H |
| (CH₂)₃CH₃ | CH₂CH₃ | (CH₂)₂CH₃ | (CH₂)₂CH₃ |
| (CH₂)₃CH₃ | CH₂CH₃ | (CH₂)₃CH₃ | H |
| (CH₂)₃CH₃ | CH₂CH₃ | (CH₂)₃CH₃ | (CH₂)₃CH₃ |
| (CH₂)₁CH₃ | CH₂CH₃ | (CH₂)₄CH₃ | H |
| (CH₂)₃CH₃ | CH₂CH₃ | (CH₂)₄CH₃ | (CH₂)₄CH₃ |
| (CH₂)₃CH₃ | CH₂CH₃ | CH₂CH=CHCH₂CH₃ | H |
| (CH₂)₃CH₃ | CH₂CH₃ | CH₂CH=CHCH₂CH₃ | CH₂CH=CHCH₂CH₃ |

TABLE I-continued

| R₁ | R₂ | R₃ | R₄ |
|---|---|---|---|
| (CH₂)₂CH₃ | (CH₂)₃CH₃ | CH₃ | H |
| (CH₂)₂CH₃ | (CH₂)₃CH₃ | CH₃ | CH₃ |
| (CH₂)₂CH₃ | (CH₂)₃CH₃ | CH₂CH₃ | H |
| (CH₂)₂CH₃ | (CH₂)₃CH₃ | CH₂CH₃ | CH₂CH₃ |
| (CH₂)₂CH₃ | (CH₂)₃CH₃ | (CH₂)₂CH₃ | H |
| (CH₂)₂CH₃ | (CH₂)₃CH₃ | (CH₂)₂CH₃ | (CH₂)₂CH₃ |
| (CH₂)₂CH₃ | (CH₂)₃CH₃ | (CH₂)₃CH₃ | H |
| (CH₂)₂CH₃ | (CH₂)₃CH₃ | (CH₂)₃CH₃ | (CH₂)₃CH₃ |
| (CH₂)₂CH₃ | (CH₂)₃CH₃ | (CH₂)₄CH₃ | H |
| (CH₂)₂CH₃ | (CH₂)₃CH₃ | (CH₂)₄CH₃ | (CH₂)₄CH₃ |
| (CH₂)₂CH₃ | (CH₂)₃CH₃ | CH₂CH=CHCH₂CH₃ | H |
| (CH₂)₂CH₃ | (CH₂)₃CH₃ | CH₂CH=CHCH₂CH₃ | CH₂CH=CHCH₂CH₃ |
| (CH₂)₃CH₃ | (CH₂)₂CH₃ | CH₃ | H |
| (CH₂)₃CH₃ | (CH₂)₂CH₃ | CH₃ | CH₃ |
| (CH₂)₃CH₃ | (CH₂)₂CH₃ | CH₂CH₃ | H |
| (CH₂)₃CH₃ | (CH₂)₂CH₃ | CH₂CH₃ | CH₂CH₃ |
| (CH₂)₃CH₃ | (CH₂)₂CH₃ | (CH₂)₂CH₃ | H |
| (CH₂)₃CH₃ | (CH₂)₂CH₃ | (CH₂)₂CH₃ | (CH₂)₂CH₃ |
| (CH₂)₃CH₃ | (CH₂)₂CH₃ | (CH₂)₃CH₃ | H |
| (CH₂)₃CH₃ | (CH₂)₂CH₃ | (CH₂)₃CH₃ | (CH₂)₃CH₃ |
| (CH₂)₃CH₃ | (CH₂)₂CH₃ | (CH₂)₄CH₃ | H |
| (CH₂)₃CH₃ | (CH₂)₂CH₃ | (CH₂)₄CH₃ | (CH₂)₄CH₃ |
| (CH₂)₃CH₃ | (CH₂)₂CH₃ | CH₂CH=CHCH₂CH₃ | H |
| (CH₂)₃CH₃ | (CH₂)₂CH₃ | CH₂CH=CHCH₂CH₃ | CH₂CH=CHCH₂CH₃ |
| (CH₂)₃CH₃ | (CH₂)₃CH₃ | CH₃ | H |
| (CH₂)₃CH₃ | (CH₂)₃CH₃ | CH₃ | CH₃ |
| (CH₂)₃CH₃ | (CH₂)₃CH₃ | CH₂CH₃ | H |
| (CH₂)₃CH₃ | (CH₂)₃CH₃ | CH₂CH₃ | CH₂CH₃ |
| (CH₂)₃CH₃ | (CH₂)₃CH₃ | (CH₂)₂CH₃ | H |
| (CH₂)₃CH₃ | (CH₂)₃CH₃ | (CH₂)₂CH₃ | (CH₂)₂CH₃ |
| (CH₂)₃CH₃ | (CH₂)₃CH₃ | (CH₂)₃CH₃ | H |
| (CH₂)₃CH₃ | (CH₂)₃CH₃ | (CH₂)₃CH₃ | (CH₂)₃CH₃ |
| (CH₂)₃CH₃ | (CH₂)₃CH₃ | (CH₂)₄CH₃ | H |
| (CH₂)₃CH₃ | (CH₂)₃CH₃ | (CH₂)₄CH₃ | (CH₂)₄CH₃ |
| (CH₂)₃CH₃ | (CH₂)₃CH₃ | CH₂CH=CHCH₂CH₃ | H |
| (CH₂)₃CH₃ | (CH₂)₃CH₃ | CH₂CH=CHCH₂CH₃ | CH₂CH=CHCH₂CH₃ |
| H | (CH₂)₄CH₃ | CH₃ | H |
| H | (CH₂)₄CH₃ | CH₃ | CH₃ |
| H | (CH₂)₄CH₃ | CH₂CH₃ | H |
| H | (CH₂)₄CH₃ | CH₂CH₃ | CH₂CH₃ |
| H | (CH₂)₄CH₃ | (CH₂)₂CH₃ | H |
| H | (CH₂)₄CH₃ | (CH₂)₂CH₃ | (CH₂)₂CH₃ |
| H | (CH₂)₄CH₃ | (CH₂)₃CH₃ | H |
| H | (CH₂)₄CH₃ | (CH₂)₃CH₃ | (CH₂)₃CH₃ |
| H | (CH₂)₄CH₃ | (CH₂)₄CH₃ | H |
| H | (CH₂)₄CH₃ | (CH₂)₄CH₃ | (CH₂)₄CH₃ |
| H | (CH₂)₄CH₃ | CH₂CH=CHCH₂CH₃ | H |
| H | (CH₂)₄CH₃ | CH₂CH=CHCH₂CH₃ | CH₂CH=CHCH₂CH₃ |
| (CH₂)₄CH₃ | H | CH₃ | H |
| (CH₂)₄CH₃ | H | CH₃ | CH₃ |
| (CH₂)₄CH₃ | H | CH₂CH₃ | H |
| (CH₂)₄CH₃ | H | CH₂CH₃ | CH₂CH₃ |
| (CH₂)₄CH₃ | H | (CH₂)₂CH₃ | H |
| (CH₂)₄CH₃ | H | (CH₂)₂CH₃ | (CH₂)₂CH₃ |
| (CH₂)₄CH₃ | H | (CH₂)₃CH₃ | H |
| (CH₂)₄CH₃ | H | (CH₂)₃CH₃ | (CH₂)₃CH₃ |
| (CH₂)₄CH₃ | H | (CH₂)₄CH₃ | H |
| (CH₂)₄CH₃ | H | (CH₂)₄CH₃ | (CH₂)₄CH₃ |
| (CH₂)₄CH₃ | H | CH₂CH=CHCH₂CH₃ | H |
| (CH₂)₄CH₃ | H | CH₂CH=CHCH₂CH₃ | CH₂CH=CHCH₂CH₃ |
| CH₃ | (CH₂)₄CH₃ | CH₃ | H |
| CH₃ | (CH₂)₄CH₃ | CH₃ | CH₃ |
| CH₃ | (CH₂)₄CH₃ | CH₂CH₃ | H |
| CH₃ | (CH₂)₄CH₃ | CH₂CH₃ | CH₂CH₃ |
| CH₃ | (CH₂)₄CH₃ | (CH₂)₂CH₃ | H |
| CH₃ | (CH₂)₄CH₃ | (CH₂)₂CH₃ | (CH₂)₂CH₃ |
| CH₃ | (CH₂)₄CH₃ | (CH₂)₃CH₃ | H |
| CH₃ | (CH₂)₄CH₃ | (CH₂)₃CH₃ | (CH₂)₃CH₃ |
| CH₃ | (CH₂)₄CH₃ | (CH₂)₄CH₃ | H |
| CH₃ | (CH₂)₄CH₃ | (CH₂)₄CH₃ | (CH₂)₄CH₃ |
| CH₃ | (CH₂)₄CH₃ | CH₂CH=CHCH₂CH₃ | H |
| CH₃ | (CH₂)₄CH₃ | CH₂CH=CHCH₂CH₃ | CH₂CH=CHCH₂CH₃ |
| (CH₂)₄CH₃ | CH₃ | CH₃ | H |
| (CH₂)₄CH₃ | CH₃ | CH₃ | CH₃ |
| (CH₂)₄CH₃ | CH₃ | CH₂CH₃ | H |
| (CH₂)₄CH₃ | CH₃ | CH₂CH₃ | CH₂CH₃ |
| (CH₂)₄CH₃ | CH₃ | (CH₂)₂CH₃ | H |
| (CH₂)₄CH₃ | CH₃ | (CH₂)₂CH₃ | (CH₂)₂CH₃ |
| (CH₂)₄CH₃ | CH₃ | (CH₂)₃CH₃ | H |
| (CH₂)₄CH₃ | CH₃ | (CH₂)₃CH₃ | (CH₂)₃CH₃ |
| (CH₂)₄CH₃ | CH₃ | (CH₂)₄CH₃ | H |

TABLE I-continued

| R₁ | R₂ | R₃ | R₄ |
|---|---|---|---|
| (CH₂)₄CH₃ | CH₃ | (CH₂)₄CH₃ | (CH₂)₄CH₃ |
| (CH₂)₄CH₃ | CH₃ | CH₂CH=CHCH₂CH₃ | H |
| (CH₂)₄CH₃ | CH₃ | CH₂CH=CHCH₂CH₃ | CH₂CH=CHCH₂CH₃ |
| CH₂CH₃ | (CH₂)₄CH₃ | CH₃ | H |
| CH₂CH₃ | (CH₂)₄CH₃ | CH₃ | CH₃ |
| CH₂CH₃ | (CH₂)₄CH₃ | CH₂CH₃ | H |
| CH₂CH₃ | (CH₂)₄CH₃ | CH₂CH₃ | CH₂CH₃ |
| CH₂CH₃ | (CH₂)₄CH₃ | (CH₂)₂CH₃ | H |
| CH₂CH₃ | (CH₂)₄CH₃ | (CH₂)₂CH₃ | (CH₂)₂CH₃ |
| CH₂CH₃ | (CH₂)₄CH₃ | (CH₂)₃CH₃ | H |
| CH₂CH₃ | (CH₂)₄CH₃ | (CH₂)₃CH₃ | (CH₂)₃CH₃ |
| CH₂CH₃ | (CH₂)₄CH₃ | (CH₂)₄CH₃ | H |
| CH₂CH₃ | (CH₂)₄CH₃ | (CH₂)₄CH₃ | (CH₂)₄CH₃ |
| CH₂CH₃ | (CH₂)₄CH₃ | CH₂CH=CHCH₂CH₃ | H |
| CH₂CH₃ | (CH₂)₄CH₃ | CH₂CH=CHCH₂CH₃ | CH₂CH=CHCH₂CH₃ |
| (CH₂)₄CH₃ | CH₂CH₃ | CH₃ | H |
| (CH₂)₄CH₃ | CH₂CH₃ | CH₃ | CH₃ |
| (CH₂)₄CH₃ | CH₂CH₃ | CH₂CH₃ | H |
| (CH₂)₄CH₃ | CH₂CH₃ | CH₂CH₃ | CH₂CH₃ |
| (CH₂)₄CH₃ | CH₂CH₃ | (CH₂)₂CH₃ | H |
| (CH₂)₄CH₃ | CH₂CH₃ | (CH₂)₂CH₃ | (CH₂)₂CH₃ |
| (CH₂)₄CH₃ | CH₂CH₃ | (CH₂)₃CH₃ | H |
| (CH₂)₄CH₃ | CH₂CH₃ | (CH₂)₃CH₃ | (CH₂)₃CH₃ |
| (CH₂)₄CH₃ | CH₂CH₃ | (CH₂)₄CH₃ | H |
| (CH₂)₄CH₃ | CH₂CH₃ | (CH₂)₄CH₃ | (CH₂)₄CH₃ |
| (CH₂)₄CH₃ | CH₂CH₃ | CH₂CH=CHCH₂CH₃ | H |
| (CH₂)₄CH₃ | CH₂CH₃ | CH₂CH=CHCH₂CH₃ | CH₂CH=CHCH₂CH₃ |
| (CH₂)₂CH₃ | (CH₂)₄CH₃ | CH₃ | H |
| (CH₂)₂CH₃ | (CH₂)₄CH₃ | CH₃ | CH₃ |
| (CH₂)₂CH₃ | (CH₂)₄CH₃ | CH₂CH₃ | H |
| (CH₂)₂CH₃ | (CH₂)₄CH₃ | CH₂CH₃ | H2CH₃ |
| (CH₂)₂CH₃ | (CH₂)₄CH₃ | (CH₂)₂CH₃ | H |
| (CH₂)₂CH₃ | (CH₂)₄CH₃ | (CH₂)₂CH₃ | (CH₂)₂CH₃ |
| (CH₂)₂CH₃ | (CH₂)₄CH₃ | (CH₂)₃CH₃ | H |
| (CH₂)₂CH₃ | (CH₂)₄CH₃ | (CH₂)₃CH₃ | (CH₂)₃CH₃ |
| (CH₂)₂CH₃ | (CH₂)₄CH₃ | (CH₂)₄CH₃ | H |
| (CH₂)₂CH₃ | (CH₂)₄CH₃ | (CH₂)₄CH₃ | (CH₂)₄CH₃ |
| (CH₂)₂CH₃ | (CH₂)₄CH₃ | CH₂CH=CHCH₂CH₃ | H |
| (CH₂)₂CH₃ | (CH₂)₄CH₃ | CH₂CH=CHCH₂CH₃ | CH₂CH=CHCH₂CH₃ |
| (CH₂)₄CH₃ | (CH₂)₂CH₃ | CH₃ | H |
| (CH₂)₄CH₃ | (CH₂)₂CH₃ | CH₃ | CH₃ |
| (CH₂)₄CH₃ | (CH₂)₂CH₃ | CH₂CH₃ | H |
| (CH₂)₄CH₃ | (CH₂)₂CH₃ | CH₂CH₃ | CH₂CH₃ |
| (CH₂)₄CH₃ | (CH₂)₂CH₃ | (CH₂)₂CH₃ | H |
| (CH₂)₄CH₃ | (CH₂)₂CH₃ | (CH₂)₂CH₃ | (CH₂)₂CH₃ |
| (CH₂)₄CH₃ | (CH₂)₂CH₃ | (CH₂)₃CH₃ | H |
| (CH₂)₄CH₃ | (CH₂)₂CH₃ | (CH₂)₃CH₃ | (CH₂)₃CH₃ |
| (CH₂)₄CH₃ | (CH₂)₂CH₃ | (CH₂)₄CH₃ | H |
| (CH₂)₄CH₃ | (CH₂)₂CH₃ | (CH₂)₄CH₃ | (CH₂)₄CH₃ |
| (CH₂)₄CH₃ | (CH₂)₂CH₃ | CH₂CH=CHCH₂CH₃ | H |
| (CH₂)₄CH₃ | (CH₂)₂CH₃ | CH₂CH=CHCH₂CH₃ | CH₂CH=CHCH₂CH₃ |
| (CH₂)₃CH₃ | (CH₂)₄CH₃ | CH₃ | H |
| (CH₂)₃CH₃ | (CH₂)₄CH₃ | CH₃ | CH₃ |
| (CH₂)₃CH₃ | (CH₂)₄CH₃ | CH₂CH₃ | H |
| (CH₂)₃CH₃ | (CH₂)₄CH₃ | CH₂CH₃ | CH₂CH₃ |
| (CH₂)₃CH₃ | (CH₂)₄CH₃ | (CH₂)₂CH₃ | H |
| (CH₂)₃CH₃ | (CH₂)₄CH₃ | (CH₂)₂CH₃ | (CH₂)₂CH₃ |
| (CH₂)₃CH₃ | (CH₂)₄CH₃ | (CH₂)₃CH₃ | H |
| (CH₂)₃CH₃ | (CH₂)₄CH₃ | (CH₂)₃CH₃ | (CH₂)₃CH₃ |
| (CH₂)₃CH₃ | (CH₂)₄CH₃ | (CH₂)₄CH₃ | H |
| (CH₂)₃CH₃ | (CH₂)₄CH₃ | (CH₂)₄CH₃ | (CH₂)₄CH₃ |
| (CH₂)₃CH₃ | (CH₂)₄CH₃ | CH₂CH=CHCH₂CH₃ | H |
| (CH₂)₃CH₃ | (CH₂)₄CH₃ | CH₂CH=CHCH₂CH₃ | CH₂CH=CHCH₂CH₃ |
| (CH₂)₄CH₃ | (CH₂)₃CH₃ | CH₃ | H |
| (CH₂)₄CH₃ | (CH₂)₃CH₃ | CH₃ | CH₃ |
| (CH₂)₄CH₃ | (CH₂)₃CH₃ | CH₂CH₃ | H |
| (CH₂)₄CH₃ | (CH₂)₃CH₃ | CH₂CH₃ | CH₂CH₃ |
| (CH₂)₄CH₃ | (CH₂)₃CH₃ | (CH₂)₂CH₃ | H |
| (CH₂)₄CH₃ | (CH₂)₃CH₃ | (CH₂)₂CH₃ | (CH₂)₂CH₃ |
| (CH₂)₄CH₃ | (CH₂)₃CH₃ | (CH₂)₃CH₃ | H |
| (CH₂)₄CH₃ | (CH₂)₃CH₃ | (CH₂)₃CH₃ | (CH₂)₃CH₃ |
| (CH₂)₄CH₃ | (CH₂)₃CH₃ | (CH₂)₄CH₃ | H |
| (CH₂)₄CH₃ | (CH₂)₃CH₃ | (CH₂)₄CH₃ | (CH₂)₄CH₃ |
| (CH₂)₄CH₃ | (CH₂)₃CH₃ | CH₂CH=CHCH₂CH₃ | H |
| (CH₂)₄CH₃ | (CH₂)₃CH₃ | CH₂CH=CHCH₂CH₃ | CH₂CH=CHCH₂CH₃ |
| (CH₂)₄CH₃ | (CH₂)₄CH₃ | CH₃ | H |
| (CH₂)₄CH₃ | (CH₂)₄CH₃ | CH₃ | CH₃ |
| (CH₂)₄CH₃ | (CH₂)₄CH₃ | CH₂CH₃ | H |
| (CH₂)₄CH₃ | (CH₂)₄CH₃ | CH₂CH₃ | CH₂CH₃ |
| (CH₂)₄CH₃ | (CH₂)₄CH₃ | (CH₂)₂CH₃ | H |
| (CH₂)₄CH₃ | (CH₂)₄CH₃ | (CH₂)₂CH₃ | (CH₂)₂CH₃ |

TABLE I-continued

| R₁ | R₂ | R₃ | R₄ |
| --- | --- | --- | --- |
| $(CH_2)_4CH_3$ | $(CH_2)_4CH_3$ | $(CH_2)_3CH_3$ | H |
| $(CH_2)_4CH_3$ | $(CH_2)_4CH_3$ | $(CH_2)_3CH_3$ | $(CH_2)_3CH_3$ |
| $(CH_2)_4CH_3$ | $(CH_2)_4CH_3$ | $(CH_2)_4CH_3$ | H |
| $(CH_2)_4CH_3$ | $(CH_2)_4CH_3$ | $(CH_2)_4CH_3$ | $(CH_2)_4CH_3$ |
| $(CH_2)_4CH_3$ | $(CH_2)_4CH_3$ | $CH_2CH=CHCH_2CH_3$ | H |
| $(CH_2)_4CH_3$ | $(CH_2)_4CH_3$ | $CH_2CH=CHCH_2CH_3$ | $CH_2CH=CHCH_2CH_3$ |

The present invention is also directed to methods of preparing the novel cyclopent-1-en-3,5-dione compounds of the invention. Preferably, the compounds are prepared by adding: (i) a cyclopentene dione compound of the formula [II]

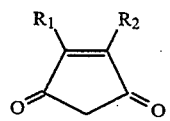

wherein R₁ and R₂ are as above; (ii) an alkyl halide and/or alkenyl halide of the formula R₅X, wherein R₅ is $CH_3$, $CH_2CH_3$, $(CH_2)_2CH_3$, $(CH_2)_3CH_3$, $(CH_2)_4CH_3$ or $CH_2CH=CHCH_2CH_3$, and X is a halogen; (iii) a carbonate; (iv) a base and (v) a phase transfer catalyst; to produce the corresponding cyclopent-1-en-3,5-dione of the formula [I].

The formula [II] compounds may be easily prepared by procedures well known to those skilled in the art, such as the procedures disclosed in Clemo et al., *J. C. S. Perkin I* 1981, 1448–1453. Preferably the formula [II] compounds wherein R₁ and/or R₂ are $CH_3$, and most preferably wherein both R₁ and R₂ are $CH_3$.

Preferably the halogen X of the alkyl halide or alkenyl halide R₅X is Cl, Br, or I, more preferably Br or I, most preferably Br. Preferably R₅X is an alkyl halide. Preferably R₅ of the alkyl halide R₅X is $(CH_2)_3CH_3$. As those skilled in the art will recognize, once armed with the present disclosure, the alkyl halide may serve as both a reactant and a solvent. Additional solvents may be employed, if desired, and will be readily apparent to those skilled in the art.

Preferably, the carbonate is lithium carbonate, potassium carbonate or sodium carbonate, more preferably, potassium carbonate or sodium carbonate, and most preferably, sodium carbonate.

Preferably, the base is sodium hydroxide or potassium hydroxide.

Phase transfer agents suitable for use in the processes include those well known in the art, such as those discussed in Frank, U.S. Pat. No. 4,877,911 and Napier et al., U.S. Pat. No. 3,992,432, the disclosures of each of which are hereby incorporated herein by reference. Preferable phase transfer agents are ammonium salts. Most preferably, the phase transfer catalyst is tetrabutyl ammonium iodide.

The reaction may be carried out in any suitable vessel which provides sufficient contacting between the reactants. The reaction vessel used should be resistant to the possible corrosive nature of the strong base. Glass-lined vessels are suitable for this purpose, as well as other vessel materials well-known in the art.

The reagents may be added to the vessel in any order, although generally the alkyl halide or alkenyl halide, the cyclopentene dione of the formula [II], and carbonate are added first, followed by addition of the base and the phase transfer agent. Ideally, the reaction is carried out at temperatures ranging from about −30° C. to about 50° C., preferably temperatures ranging from about 10° C. to about 20° C., and most preferably at temperatures ranging from about 15° C. to about 20° C.

The pressure at which the reaction is carried out is not critical. If the reaction is carried out in a sealed vessel, autogenous pressure is acceptable, although higher or lower pressure, if desired, may be employed. The reaction may also be carried out at atmospheric pressure in an open reaction vessel, in which case, the vessel is preferably equipped with a moisture trap to prevent significant exposure of the base to moisture. The reaction may take place in an oxygen atmosphere or an inert atmosphere, as in the presence of a gas such as nitrogen, argon, and the like, the type of atmosphere also not being critical.

In general, the molar proportions of the reagents employed in the present preferred preparatory process can be varied over a relatively wide range. The amount of the reactants will depend in part upon the specific formula [II] cyclopentene dione starting material used, the particular alkyl halide or alkenyl halide employed, and other reaction conditions such as time, temperature, pressure, etc. The particular amount to be employed will be well within the ambit of those skilled in the art, once armed with the present disclosure. By way of general guidance, however, a ratio of about 1 mole of cyclopentene dione to about 5–10 moles of alkyl halide or alkenyl halide to about 5–10 moles of carbonate to about 5–10 moles of base to about 0.01 moles of phase transfer catalyst may be used. Preferably, a ratio of about 1 mole of cyclopentene dione to about 5 moles of alkyl halide or alkenyl halide to about 5 moles of carbonate to about 5 moles of base to about 0.01 moles of phase transfer catalyst is used.

Reaction time is generally rather short and is often dictated by the type of equipment employed. Sufficient time should be provided, however, for thorough contacting of the cyclopentene dione of the formula [II] with the alkyl halide or alkenyl halide, the base, the carbonate and the phase transfer agent. Generally, the reaction time is from about 1–8 hours, preferably from about 1–5 hours, more preferably from about 1–3 hours.

Product can be recovered from the reaction mixture by filtering off solid inorganic material. The resultant product is generally a mixture of the alkyl halide or alkenyl halide, phase transfer agent, and the desired product, such as 1,2-dimethyl-4-butyl-cyclopent-1-en-3,5-dione and 1,2-dimethyl-4,4-dibutyl-cyclopent-1-en-3,5-dione. Product of varying degrees of purity can be obtained by subjecting the reaction mixture to fractional distillation, commercial chromatographic separation, combinations thereof, or other separation means well known to one skilled in the art.

The compounds of the invention can be used alone or in combination with one or more ingredients to provide a floral-type fragrance composition such as a jasmine-type fragrance. Also, more than one compound of the invention can be used in compositions of the invention. For example, 1,2-dimethyl-4-butyl-cyclopent-1-en-3,5-dione and 1,2-dimethyl-4,4-dibutyl-cyclopent-1-en-3,5-dione may be used together.

The compounds of the invention may be used as olfactory components in anionic, cationic, non-ionic and zwitterionic detergents, soaps, fabric softener compositions, fabric softener articles for use in clothes dryers, space odorants and deodorants, perfumes, colognes, toilet water, toiletries, bath preparations, deodorants, cosmetics, hand lotions, sunscreens, powders, as well as in other ways. The amount of the compound to be used in modifying the olfactory properties of the compositions (that is, augmenting, enhancing or improving the aroma of such compositions), will vary depending upon the particular use intended and the particular compound employed, as will be readily apparent to those skilled in the art. Although they may be present in major or minor amounts, preferably, because of the strength of their odor, the compounds of the present invention are generally employed as a minor ingredient, that is, an amount of about 0.01% by weight of the perfumed article, preferably about 0.05% by weight, up to about 30% by weight of the perfumed article, and most preferably about 0.1% by weight up to about 5.0% by weight of the perfumed article. Within these basic parameters, the olfactorily effective amount (that is, the amount of the compound effective to modify, augment, enhance or improve the aroma of a composition) will be well within the ambit of one skilled in the art, once armed with the present disclosure.

The fragrance compositions of the invention may, if desired, contain a vehicle or carrier (as used herein the term "carrier" shall be considered synonymous with the term "vehicle"). Such carriers include liquids such as a non-toxic alcohol, a non-toxic glycol, or the like. An example of a non-toxic glycol is 1,2-propylene glycol. Alternatively, the carrier can be an absorbent solid such as a gum, e.g., gum arabic, xantham gum or guar gum, or components for encapsulating a composition such as gelatin, by means of coacervation or such as a urea formaldehyde polymer whereby a polymeric shell is formed around a liquid perfume oil center. The amount of the vehicle or carrier will vary depending upon the particular use intended, as will be readily apparent to those skilled in the art. However, the vehicle or carrier can generally be employed in an amount of about 5% by weight up to about 95% by weight of the fragrance composition.

The fragrance compositions may, if desired, contain other perfumery materials. Typical additional perfumery materials which may form part of compositions of the invention include: natural essential oils such as lemon oil, mandarin oil, clove leaf oil, petitgrain oil, cedar wood oil, patchouli oil, lavandin oil, neroli oil, ylang oil, rose absolute or jasmine absolute; natural resins such as labdanum resin or olibanum resin; single perfumery chemicals which may be isolated from natural sources or manufactured synthetically, as for example, alcohols such as geraniol, nerol, citronellol, linalol, tetrahydrogeraniol, betaphenylethyl alcohol, methyl phenyl carbinol, dimethyl benzyl carbinol, menthol or cedrol; acetates and other esters derived from such alcohols; aldehydes such as citral, citronellal, hydroxycitronellal, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; synthetic musks such as musk xylene, musk ketone and ethylene brassylate; and other materials commonly employed in the art of perfumery. Typically at least five, and usually at least ten, of such materials will be present as components of the active ingredient. The amount of the additional perfumery material will vary depending upon the particular perfumery material employed and use intended, as will be apparent to those skilled in the art.

Fragrance compositions and preparatory techniques are well known in the art, and are disclosed, for example, in W. A. Poucher, *Soap, Perfumery and Cosmetics*, published by the author (Montclair) (7th ed. 1959); and S. Arctander, *Perfume and Flavour Materials of Natural Origin*, self-published (Elizabeth, N.J.) (1960), the disclosures of which are hereby incorporated by reference, in their entirety.

The present invention is further described in the following example. This example is not to be construed as limiting the scope of the appended claims.

EXAMPLE 1

The compound 1,2-dimethyl-4-butyl-cyclopent-1-en-3,5-dione, a compound of formula [I], was prepared from 1,2-dimethyl-cyclopent-1-en-3,5-dione, a compound of formula [II], as follows. First, 1,2-dimethyl-cyclopent-1-en-3,5-dione was prepared by substantially following the procedures of Clemo et al., *J. C. S. Perkin I* 1981, 1448–1453. Next, 0.53 g of 1,2-dimethyl-cyclopent-1-ene-3,5-dione was dissolved in 7 milliliters of butyl bromide. Then 1.75 g of solid sodium carbonate and 0.05 g of tetra-butyl-ammonium iodide were added. Next, 0.6 g of powdered sodium hydroxide was added to the reaction mixture. The reaction was stirred at room temperature (15° C.–20° C.) for 2 hours. The reaction mixture was then filtered through Celite TM (Aldrich, U.K.) to remove solids and the Celite TM was washed with dichloromethane. The solvent was removed under pressure to give a residue weighing 1.19 g. The crude product was purified by column chromatography over silica, eluting with a 9:1 hexane:ether mixture and collecting 25 ml fractions.

The 1,2-dimethyl-4-butyl-cyclopent-1-en-3,5-dione compound (Rf value 0.12/UV active) was isolated from the fifth and sixth fractions by removal of solvent and a kugelrohr distillation. The distillate (b.p. 115° C.–117° C. at 2 mm Hg) weighed 0.34 g, providing a yield of 42%. The structure of the resulting compounds was confirmed by gas chromatography, mass spectrometry and nuclear magnetic resonance.

The spectral data for the compound 1,2-dimethyl-4-butyl-cyclopent-1-en-3,5-dione using $^{13}$C NMR was as follows:

$^{13}$CNMR(CDCl$_3$) $\delta$205, 156, 48, 29, 14, 9

The spectral data for the compound 1,2-dimethyl-4-butyl-cyclopent-1-en-3,5-dione using $^1$H NMR was as follows:

$^1$HNMR(CDCl$_3$) $\delta$2.59(t,1H, J=6.2 H$_z$), 2.01(bs,6H), 1.75(m,2H), 1.28(m,4H), 0.88(m,3H)

The infrared spectroscopic data for the compound 1,2-dimethyl-4-butyl-cyclopent-1-en-3,5-dione was as follows:

1700 cm$^{-1}$ (s, C=O)

EXAMPLE 2

The compound 1,2-dimethyl-4,4-dibutyl-cyclopent-1-en-3,5-dione, a compound of formula [I], was prepared as follows. First, 0.3 gm of 1,2-dimethyl-cyclopent-1-en-3,5-dione was dissolved in 5 ml of butyl bromide. To the resulting solution 0.6 gm sodium carbonate and 0.1 gm of tetra butyl ammonium iodide was added and the mixture was stirred at room temperature (15° C.–20° C.) for 4 hours.

The reaction mixture was filtered to remove the inorganic solids. The filtrate was diluted with dichloromethane and washed first with 2M HCl and finally with water. The organic phase was dried and concentrated. The crude product was purified by column chromatography over silica, eluting with a 9:1 hexane:ether mixture. The product 1,2-dimethyl-4,4-dibutyl-cyclopent-1-en-3,5-dione (b.p. 130° C. at 2 mm Hg) was isolated from fractions 2 and 3 by removal of solvent and a Kugelrohr distillation. The structure of the resulting compound was confirmed by gas chromatography, mass spectrometry and nuclear magnetic resonance.

The spectral data for the compound 1,2-dimethyl-4,4-dibutyl-cyclopent-1-en-3,5-dione using $^{13}$C NMR was as follows:

$^{13}$CNMR(CDCl$_3$) δ9, 155, 208, 53, 34, 26, 23, 13

The spectral data for the compound 1,2-dimethyl-4,4-dibutyl-cyclopent-1-en-3,5-dione using $^1$H NMR was as follows:

$^1$HNMR(CDCl$_3$) δ2.05(6H),1.6(m,4H),1.2(m,4H), 1.2(m,4H) 0.92(m,4H), 0.79(t,J=7.2 H$_z$, 6H)

The infrared spectroscopic data for the compound 1,2-dimethyl-4,4-dibutyl-cyclopent-1-en-3,5-dione was as follows:

1700 cm$^{-1}$ (s, C=O)

The disclosures of each patent and publication cited or described herein are hereby incorporated herein by reference, in their entirety.

Various modifications of the invention, in addition to those shown and described herein, will be readily apparent to those skilled in the art from the foregoing description. Such modifications are also intended to fall within the scope of the appended claims.

What is claimed is:

1. A compound of the formula

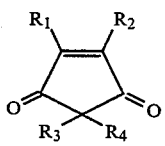

wherein
$R_1$ is H, CH$_3$, CH$_2$CH$_3$, (CH$_2$)$_2$CH$_3$, (CH$_2$)$_3$CH$_3$ or (CH$_2$)$_4$CH$_3$ provided $R_1$ and $R_2$ are not both H;
$R_2$ is H, CH$_3$, CH$_2$CH$_3$, (CH$_2$)$_2$CH$_3$, (CH$_2$)$_3$CH$_3$ or (CH$_2$)$_4$CH$_3$ provided $R_1$ and $R_2$ are not both H;
$R_3$ is H, (CH$_2$)$_3$CH$_3$, (CH$_2$)$_4$CH$_3$ or CH$_2$CH=CHCH$_2$CH$_3$; and
$R_4$ is H, (CH$_2$)$_3$CH$_3$, (CH$_2$)$_4$CH$_3$ or CH$_2$CH=CHCH$_2$CH$_3$;
provided that when one of $R_3$ or $R_4$ is H, then the other of $R_3$ or $R_4$ is (CH$_2$)$_3$CH$_3$, (CH$_2$)$_4$CH$_3$ or CH$_2$CH=CHCH$_2$CH$_3$.

2. A compound of claim 1 wherein $R_1$ and $R_2$ are CH$_3$.

3. A compound of claim 1 wherein $R_3$ and $R_4$ are (CH$_2$)$_3$CH$_3$.

4. A compound of claim 1 selected from the group consisting of 1,2-dimethyl-4-butyl-cyclopent-1-en-3,5-dione and 1,2-dimethyl-4,4-dibutyl-cyclopent-1-en-3,5-dione.

5. A compound of claim 4 which is 1,2-dimethyl-4-butyl-cyclopent-1-en-3,5-dione.

6. A composition comprising at least two compounds of the formula

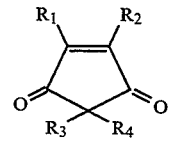

wherein
$R_1$ is H, CH$_3$, CH$_2$CH$_3$, (CH$_2$)$_2$CH$_3$, (CH$_2$)$_3$CH$_3$ or (CH$_2$)$_4$CH$_3$ provided $R_1$ and $R_2$ are not both H;
$R_2$ is H, CH$_3$, CH$_2$CH$_3$, (CH$_2$)$_2$CH$_3$, (CH$_2$)$_3$CH$_3$ or (CH$_2$)$_4$CH$_3$ provided $R_1$ and $R_2$ are not both H;
$R_3$ is H, (CH$_2$)$_3$CH$_3$, (CH$_2$)$_4$CH$_3$ or CH$_2$CH=CHCH$_2$CH$_3$; and
$R_4$ is H, (CH$_2$)$_3$CH$_3$, (CH$_2$)$_4$CH$_3$ or CH$_2$CH=CHCH$_2$CH$_3$;
provided that when one of $R_3$ or $R_4$ is H, then the other of $R_3$ or $R_4$ is (CH$_2$)$_3$CH$_3$,(CH$_2$)$_4$CH$_3$ or CH$_2$CH=CHCH$_2$CH$_3$.

7. A composition of claim 6 wherein the compounds are 1,2-dimethyl-4-butyl-cyclopent-1-en-3,5-dione and 1,2-dimethyl-4,4-dibutyl-cyclopent-1-en-3,5-dione.

8. A fragrance composition comprising a compound of the formula

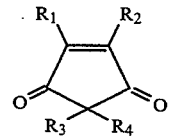

wherein
$R_1$ is H, CH$_3$, CH$_2$CH$_3$, (CH$_2$)$_2$CH$_3$, (CH$_2$)$_3$CH$_3$ or (CH$_2$)$_4$CH$_3$ provided $R_1$ and $R_2$ are not both H;
$R_2$ is H, CH$_3$, CH$_2$CH$_3$, (CH$_2$)$_2$CH$_3$, (CH$_2$)$_3$CH$_3$ or (CH$_2$)$_4$CH$_3$ provided $R_1$ and $R_2$ are not both H;
$R_3$ is H, (CH$_2$)$_3$CH$_3$, (CH$_2$)$_4$CH$_3$ or CH$_2$CH=CHCH$_2$CH$_3$; and
$R_4$ is H, (CH$_2$)$_3$CH$_3$, (CH$_2$)$_4$CH$_3$ or CH$_2$CH=CHCH$_2$CH$_3$;
provided that when one of $R_3$ or $R_4$ is H, then the other of $R_3$ or $R_4$ is (CH$_2$)$_3$CH$_3$, or CH$_2$CH=CHCH$_2$CH$_3$; in combination with at least one of a carrier and additional perfumery material.

9. The fragrance composition of claim 8 wherein said compound is selected from the group consisting of 1,2-dimethyl-4-butyl-cyclopent-1-en-3,5-dione and 1,2-dimethyl-4,4-dibutyl-cyclopent-1-en-3,5-dione.

10. The fragrance composition of claim 8 wherein the compound is 1,2-dimethyl-4-butyl-cyclopent-1-en-3,5dione.

11. The fragrance composition of claim 8 comprising at least two of said compounds.

12. The fragrance composition of claim 11 wherein the compounds are 1,2-dimethyl-4-butyl-cyclopent-1-en-3,5-dione and 1,2-dimethyl-4,4-dibutyl-cyclopent-1-en-3,5-dione.

13. A method of modifying the olfactory properties of a composition comprising adding thereto an olfactorily effective amount of a compound of the formula

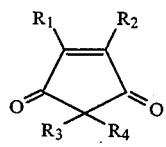

wherein $R_1$ is H, $CH_3$, $CH_2CH_3$, $(CH_2)_2CH_3$, $(CH_2)_3CH_3$ or $(CH_2)_4CH_3$ provided $R_1$ and $R_2$ are not both H;

$R_2$ is H, $CH_3$, $CH_2CH_3$, $(CH_2)_2CH_3$, $(CH_2)_3CH_3$ or $(CH_2)_4CH_3$ provided $R_1$ and $R_2$ are not both H;

$R_3$ is H, $(CH_2)_3CH_3$, $(CH_2)_4CH_3$ or $CH_2CH=CHCH_2CH_3$; and $R_4$ is H, $(CH_2)_3CH_3$, $(CH_2)_4CH_3$ or $CH_2CH=CHCH_2CH_3$;

provided that when one of $R_3$ or $R_4$ is H, then the other of $R_3$ or $R_4$ is $(CH_2)_3CH_3$, $(CH_2)_4CH_3$ or $CH_2CH=CHCH_2CH_3$.

14. The method of claim 13 wherein the compound is selected from the group consisting of 1,2-dimethyl-4-butyl-cyclopent-1-en-3,5-dione and 1,2-dimethyl-4,4-dibutyl-cyclopent-1-en-3,5-dione.

15. The method of claim 13 wherein the compound is 1,2-dimethyl-4-butyl-cyclopent-1-en-3,5-dione.

16. The method of claim 13 comprising at least two of said compounds.

17. The method of claim 16 wherein said compounds are 1,2-dimethyl-4-butyl-cyclopent-1-en-3,5-dione and 1,2-dimethyl-4,4-dibutyl-cyclopent-1-en-3,5-dione.

* * * * *

UNITED STATES PATENT AND TRADEMARK OFFICE
CERTIFICATE OF CORRECTION

PATENT NO. : 5,407,910
DATED     : April 18, 1995
INVENTOR(S) : Benjamin O. Isaac, Chat O. Chan, and Ian M. Marr It is certified that error appears in the above-indentified patent and that said Letters Patent is hereby corrected as shown below:

Column 17, line 62, delete the space after "$(CH_2)$", and before "$)_4CH_3$".

Column 17, line 64, delete the space after "$(CH_2)$", and before "$)_4CH_3$".

Column 18, line 32, insert a space after "$(CH_2)_3CH_3$," and before "$(CH_2)_4CH_3$".

Column 18, line 52, delete the space after "$(CH_2)_3CH_3$", and before ",".

Column 18, line 57, insert --$(CH_2)_4CH_3$-- after "$(CH_2)_3CH_3$,".

Column 18, line 66, delete "3,5dione" and insert --3,5-dione-- therefor.

Signed and Sealed this

Eighteenth Day of July, 1995

Attest:

BRUCE LEHMAN

*Attesting Officer*     *Commissioner of Patents and Trademarks*